United States Patent
Fuhrer

(10) Patent No.: US 9,108,870 B2
(45) Date of Patent: Aug. 18, 2015

(54) METHODS FOR THE REMEDIATION OF ALGAL BLOOMS

(71) Applicant: John P. Fuhrer, Newport Beach, CA (US)

(72) Inventor: John P. Fuhrer, Newport Beach, CA (US)

( * ) Notice: Subject to any disclaimer, the term of this patent is extended or adjusted under 35 U.S.C. 154(b) by 0 days.

(21) Appl. No.: 14/223,845

(22) Filed: Mar. 24, 2014

(65) Prior Publication Data

US 2014/0197114 A1      Jul. 17, 2014

Related U.S. Application Data

(62) Division of application No. 13/352,325, filed on Jan. 17, 2012, now Pat. No. 8,685,888.

(60) Provisional application No. 61/433,510, filed on Jan. 17, 2011.

(51) Int. Cl.

| | |
|---|---|
| *A01N 43/36* | (2006.01) |
| *A01N 25/00* | (2006.01) |
| *A01P 21/00* | (2006.01) |
| *C02F 1/68* | (2006.01) |
| *C02F 1/50* | (2006.01) |
| *A01N 61/00* | (2006.01) |
| *A01N 63/02* | (2006.01) |
| *C02F 103/00* | (2006.01) |

(52) U.S. Cl.
CPC . *C02F 1/68* (2013.01); *A01N 61/00* (2013.01); *A01N 63/02* (2013.01); *C02F 1/50* (2013.01); *C02F 2103/007* (2013.01)

(58) Field of Classification Search
None
See application file for complete search history.

(56) References Cited

U.S. PATENT DOCUMENTS

| | | | | |
|---|---|---|---|---|
| 5,679,364 | A * | 10/1997 | Levy | 424/405 |
| 6,383,506 | B1 * | 5/2002 | Mehta et al. | 424/408 |
| 2005/0233074 | A1 * | 10/2005 | Dalziel et al. | 427/212 |

OTHER PUBLICATIONS

Stadnichuk, I.N., "Phycobiliproteins: Determination of Chromophore Composition and Content", Phytochemical Analysis, vol. 6, pp. 281-288, 1995.*
McDaniel, "Photosynthetic Pigments", pp. 1-4, <http://www2.mcdaniel.edu/Biology/botf99/photo/p3igments.html>, Aug. 2009.*
MSDS, "Corn Starch Maize Starch MSDS Sheet", pp. 1-5, <http://mubychem.com/MSDS/Maizestarch_Cornstarch%20MSDS.htm>, last updated Jan. 29, 2013.*

* cited by examiner

*Primary Examiner* — Tracy Vivlemore
*Assistant Examiner* — Monica Shin
(74) *Attorney, Agent, or Firm* — Alford Law Group, Inc.; William E. Alford; Vy H. Vu

(57) ABSTRACT

In one embodiment, a remediation agent and method of remediation of an algae bloom are disclosed. The remediation agent contains light absorbing compounds in a buoyant water semi-insoluble and biodegradable casein product. The remediation agent may be distributed by boat or seeded by airplane to remediate or prevent algae blooms.

9 Claims, 5 Drawing Sheets

METHODS FOR THE REMEDIATION OF ALGAL BLOOMS

CROSS REFERENCE TO RELATED APPLICATIONS

This non-provisional patent application is a division of, incorporates by reference, and claims the benefit of U.S. Non-provisional patent application Ser. No. 13/352,325 entitled "METHOD AND AGENT FOR THE REMEDIATION OF ALGAL BLOOMS" filed on Jan. 17, 2012 by inventor John Peter Fuhrer which in turn claims the benefit of U.S. Provisional Patent Application No. 61/433,510 entitled "METHOD AND AGENT FOR THE REMEDIATION OF ALGAL BLOOMS" filed on Jan. 17, 2011 by inventor John Peter Fuhrer.

FIELD

Aspects of the invention generally relate to a method and composition of matter for the lethal treatment of toxic algae blooms. More specifically, aspects of the invention relate to a method and a composition of matter for destruction of toxic algae utilizing a light absorbing material that absorbs the critical wavelengths of light required for the growth of toxic algae in a biodegradable product capable of being distributed over a large target area.

BACKGROUND

Single-celled, microscopic algae naturally occur in the surface layer of all aquatic environments. These plant-like organisms, known as microalgae or phytoplankton, form the base of the food web upon which nearly all other marine organisms depend. An algae bloom occurs when estuarine, marine, or fresh water algae accumulate rapidly and form dense patches that may be visible near the surface of water.

Certain species of phytoplankton contain photosynthetic pigments that vary in color from green to brown to red. When algae are present in high concentration, the water appears to be discolored or murky, varying in color from white to almost black, often being red or brown. "Red Tide" is a common name for algae blooms, however, not all algae blooms are dense enough to cause water discoloration, and not all algae blooms are red.

Algae blooms typically involve the rapid growth of a single species of phytoplankton in an area generally because of an increase in algae nutrients such as nitrogen and phosphorous. Only a small number of the thousands of species of marine phytoplankton are known to be harmful or toxic. Red Tides are often caused by a species of phytoplankton known as *karenia brevis*. Algae blooms of *karenia brevis* may occur along coastal waters. The density of these organisms during an algae bloom can exceed tens of millions of cells per liter of seawater, and often discolors the water a deep reddish-brown hue.

Harmful Algae Blooms are associated with wildlife mortalities among marine and coastal species of fish, birds, marine mammals and other organisms. These mortalities are caused by exposure to various toxins produced by harmful phytoplankton.

The dinoflagellate *Alexandrium fundyense*, produces saxitoxin, the neurotoxin responsible for paralytic shellfish poisoning. The dinoflagellate *Karenia brevis*, produces brevetoxin, the neurotoxin responsible for neurotoxic shellfish poisoning. Brevetoxin, a potent neurotoxin, has been known to kill even large mammals such as bottlenose dolphins. California coastal waters also experience seasonal blooms of *Pseudo-nitzschia*, a diatom known to produce domoic acid, the neurotoxin responsible for amnesic shellfish poisoning.

Phytoplankton toxins become concentrated in filter feeding marine organisms when they consume large quantities of toxic plankton. These filter feeders include shellfish, finfish, baleen whales, crustaceans and benthic invertebrates. Mussels, clams, oysters, and abalones collected in areas affected by algae blooms can be dangerous for human consumption, leading to closure of shellfish beds for harvesting. Toxic algae blooms cause millions of dollars of damage annually to sea food producing communities and to the farmed sea food industry.

Generally an increase of nutrients, such as nitrogen and phosphates, in an aquatic environment promotes the rapid growth of simple algae or plankton. The rapid growth of algae and plankton, however, is unsustainable. Oxygen depletion of the water column (hypoxia) can occur from excessive phytoplankton respiration. The eventual die-off of the algae and their resulting degradation by bacteria may cause anoxia, a condition in which the decaying algae use up dissolved oxygen causing fish and other marine animals to suffocate.

Chemical treatment of algae blooms has been attempted using copper sulfate (bluestone) and chelated copper compounds as algaecides. Such chemicals have their own restrictions and toxicity to marine animals. Besides being toxic, algaecides may indiscriminately kill off non-blooming algae essential to the eco-system. Other treatments have involved deploying powdered clay over a bloom to adsorb and sink the toxic algae. Clay treatment, however, indiscriminately kills other organisms in the environment.

Biological treatment of an algae bloom may include introducing algae eating species of fish such as grass carp or silver carp. However, introducing a non-native species of fish may be detrimental to the local eco-system and should be used with extreme caution.

Mechanically filtering an algae bloom may also be a viable treatment but requires manpower and filtering equipment.

Thus what is needed are methods and agents for treating algae blooms that are more effective and environmentally friendly. The desired agents could be deployed over sensitive eco-systems quickly and relatively inexpensively.

BRIEF SUMMARY

Certain aspects of the invention are summarized by the claims.

Figure 1:
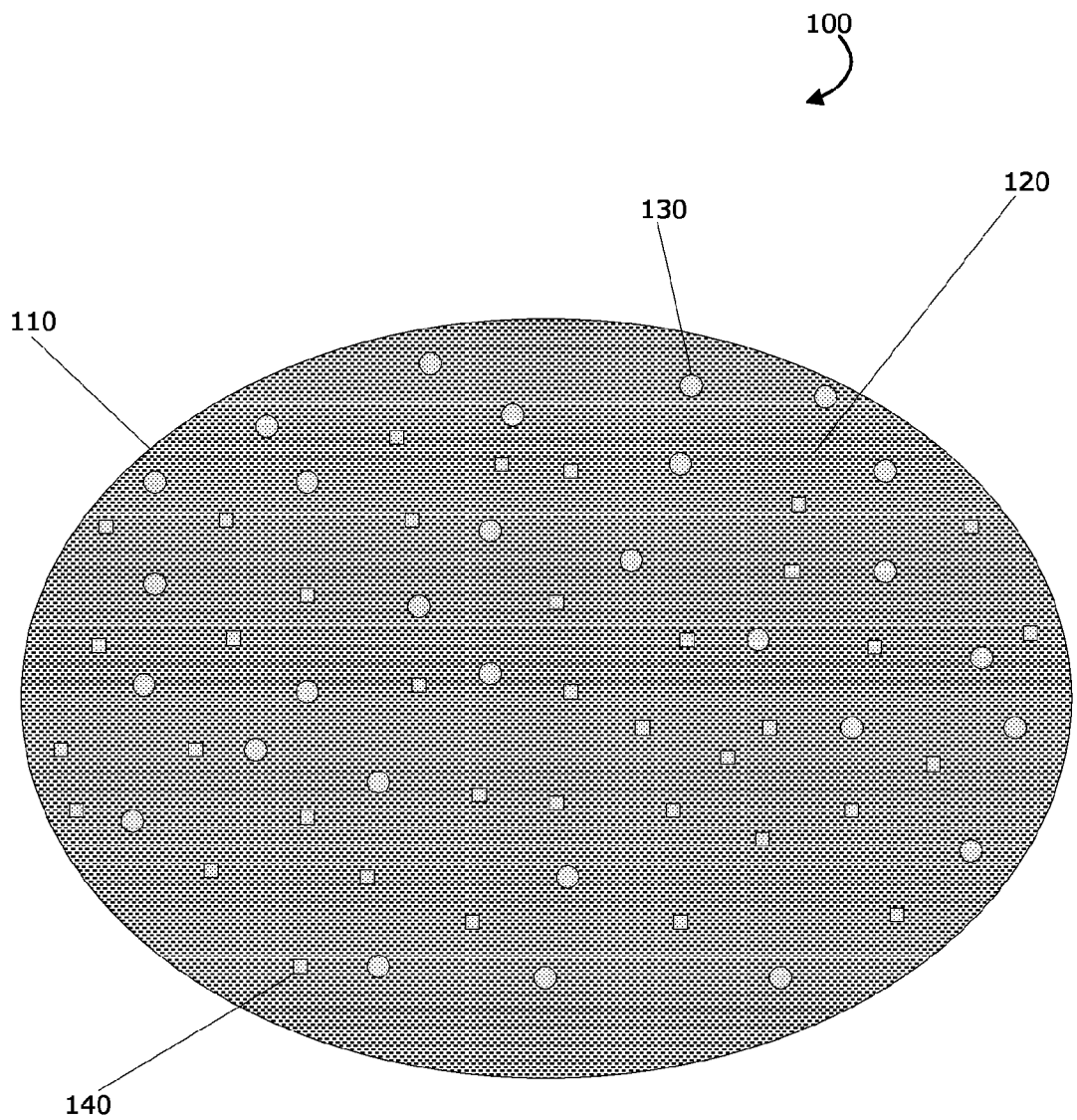
FIG. 1 is an enlarged top view of an embodiment of the invention illustrating a protein product containing light absorbing elements with air pockets suspended in the protein product.

The figures are not drawn to scale so that elements, features, and surface structure may be shown by example and are intended merely to be illustrative and non-limiting of the aspects of the invention that are claimed.

DETAILED DESCRIPTION

This detailed description describes exemplary implementations that are illustrative of aspects of the invention, and so it is explanatory and not limiting. The claims define inventive aspects. In the drawings, some elements have been omitted to more clearly show inventive aspects.

INTRODUCTION

Phytoplankton, are the autotrophic component of the plankton community Like land plants, phytoplankton obtain energy through photosynthesis, and so usually live in the well-lit surface layer (termed the euphotic zone) of an ocean, sea, or lake. Phytoplankton absorb sun light at specific wavelengths in order to conduct photosynthesis. Without light at the required wavelengths, photosynthetic organisms die.

The surface of the water reflects some sunlight. The non-reflected descending light is absorbed by the water or particles of matter in the water. At increasing depths of water, the intensity of the light decreases due to absorption. However, not all frequencies are absorbed equally. Red wavelengths of light are absorbed at the fastest rate with increasing depth followed by orange, yellow, green, blue and indigo wavelengths of light. Red frequencies or wavelengths of light do not travel far below the surface of water before being absorbed. Frequencies or wavelengths of light ranging in the blue and green spectrum penetrate further into water.

Several classes of algae have evolved with different light absorbing pigments to take advantage of the different absorption depths of various wavelengths of light. From the surface to depths of 6 meters (~20 feet), where the proportion of red light is the highest, the dominant group may be green algae, which have the same photosynthetic pigments as land plants.

Between 6 m to 30 m (~20 ft to 100 ft), where yellow light abounds, brown algae may dominate. At depths below 35 m (~116 ft), red algae are abundant because of the abundance of green light. These algae have phycoerithrin, a red pigment that makes the absorption of green light possible.

There are species of algae that are the exception to these rules. Cladophora, one of the most common green algae, can grow at depths of 80 m (~266 ft). Furthermore, some algae change pigments depending on the light they are exposed to. Oscillatoria, a photosynthetic blue-green algae, turns green-bluish in red light, because it produces the blue pigment phycocyanin. However, when exposed to green or blue light, it turns red because it can synthesize the red pigment phycoerithrin.

Remediation Agent

A remediation agent and methods for algae bloom remediation using said agent are disclosed. Specifically, a method and agent for treating algae blooms is disclosed using a buoyant biodegradable protein wafer containing proteins engineered to absorb light at wavelengths utilized by algae. The biodegradable thin wafer or flake can be distributed from boats or seeded from aircraft for the remediation of harmful algal blooms.

Referring now to FIG. 1, an embodiment of a remediation agent 100 is illustrated. The remediation agent 100, a composition of matter, includes a product 110, light absorbing compound 120, and one or more air pockets or bubbles 130. The light absorbing compound 120 may be adapted to block a range of frequencies or wavelengths of light used by algae for photosynthesis. The remediation agent 100 may be deployed at a target site where an algae bloom has occurred, is occurring, or is likely to occur.

The product 110 is preferably biodegradable, non-toxic, water semi-insoluble and easily manufactured. The air pockets or bubbles 130 may be suspended in the product 110 to aid in buoyancy of the remediation agent 100 and float it over algae located near the surface of water. Alternatively, an inert material (e.g., sand, silt, mud, sediment etc.) with a specific gravity greater than water may be used to sink the remediation agent to algae located at various depths below the surface of the water.

In one embodiment of the invention, the product 110 is a casein product. Casein is a water soluble biodegradable protein found in mammalian milk. When in milk, casein occurs as a suspension of particles called micelles. A typical micelle in aqueous solution forms an aggregate with the hydrophilic "head" regions in contact with surrounding solvent, sequestering the hydrophobic single tail regions in the micelle center.

Casein may be isolated from milk by several methods. Casein can be precipitated from milk by an enzymatic method or by a mild acid treatment method, for example.

It may be desirable to make the proteins that comprise this product semi-insoluble in water so that the product will slowly dissolve in water over a predetermined period of time. The protein product is ultimately digested by natural environmental organisms.

Various methods may be used to produce semi-insoluble protein material that can be formed into shapes and can be made to contain many types of components. One such method for casein protein is described in U.S. Pat. No. 6,379,726 issued to Peggy Tomasula on Apr. 30, 2002 and U.S. Patent Application Pub. No. 2004/0018294 filed by Peggy Tomasula on Feb. 10, 1999, both of which are incorporated herein by reference. Alternatively, other methods may be used to link or cross-link proteins, such as by a chemical approach, an aging approach, or some other molecule alignment process so the protein molecules are aligned or aggregated so as to resist being fully soluble in water and thus allow a predetermined period of time for the product to function as a remediation agent before dissolving into water and/or biodegrading.

The casein product 110 may be formed into any shape. In one embodiment of the invention the casein product 110 may take the shape of a disc. The discs may be a small, substantially flat, thin circular shape. Although the casein product 110 is described and illustrated as a disc, the scope of the invention covers other shapes.

Casein is biodegradable and non-toxic. In a semi-insoluble form, the casein product 110 will eventually degrade or dissolve in water. Casein product 110 deployed at an algae bloom site will eventually biodegrade without the need for labor intensive cleaning. Unlike algaecides which may be toxic to marine life, casein is an edible milk protein and thus less likely to harm marine life that may contact or eat the casein.

While the product 110 has been described as being formed of casein protein, the product may be formed of other proteins, such as soy protein, that may be made semi-insoluble and absorb or suspend the light absorbing compounds. Methods may be used to link or cross-link proteins, such as by a chemical approach, an aging approach, or some other molecule alignment process so the protein molecules are aligned to resist being readily soluble in water and allow a predetermined period of time for the light absorbing compound 120 to inhibit algae photosynthesis before dissolving into water and/or biodegrading.

Light absorbing compound 120 may be created by chemically attaching prosthetic organic molecules to protein backbones. These organic molecules are referred to as "prosthetic organic molecules" because they are not native or natural components of the protein backbones, but are added chemically after the proteins are synthesized. Such prosthetic organic molecules are chemically synthesized and attached to the protein backbones by standard chemical reactions common in the field of chemistry. Light absorbing compound 120 may be chemically analogous to the antennae structures in natural proteins such as the phycobilins in photosynthestic algae or the light absorbing antennae in synthetic fluorescent proteins. Light absorbing compound 120 is preferably biodegradable and engineered to absorb light at the critical wavelengths used by algae.

The prosthetic organic molecules contained in light absorbing compound 120 may be chromophores, a.k.a. pigments, molecules that absorb certain wavelengths of light and reflect other wavelengths of light. An example of a prosthetic organic molecule is carotenoid pigment which absorbs blue and green light. Another is the phycocyanin pigment which absorbs orange and red light. The prosthetic organic molecule may be engineered to absorb substantially the same wavelength of light as algae being remediated. For example, cyanobacteria or blue green algae uses chlorophyll a to absorbs and process light in photosynthesis. Chlorophyll a absorbs energy from the violet-blue and reddish orange-red wavelengths. To remediate a bloom of cyanobacteria, wavelengths between 430 nm and 650 nm would need to be absorbed by the light absorbing compound 120. Thus, to remediate cyanobacteria, chromophores such as carotenoid and phycocyanin pigments may be attached to a protein backbone to make light absorbing compound 120. Light absorbing compound 120 would be added to product 110 with one or more optional air pockets 130 to create remediation agent 100. Remediation agent 100 may be dispersed over the cyanobacteria bloom to inhibit photosynthesis and eventually destroy the algae bloom.

Although, the embodiment of the invention described above preferably contains a biodegradable prosthetic organic molecule used as a chromophore, other light absorbing materials such as metal complex chromophores or nonorganic compositions may be used. Similarly, although air pockets 130 are shown allowing the remediation agent 100 to float at the surface of the water, its buoyancy may be varied to float at different depths. Air pocket 130 may also be filled with different gasses such as nitrogen, helium, hydrogen, oxygen, methane, and ammonia.

Methods of Delivery

The invention may be deployed to remediate an algae bloom by aerial dispersal, shipboard dispersal, or even by hand. Use of aerial dispersal may be preferred in remote areas where ships may take days or weeks to respond to an algae bloom. However, the use of ships may be preferred where large quantities of the remediation agent 100 may be used.

Figure 2:
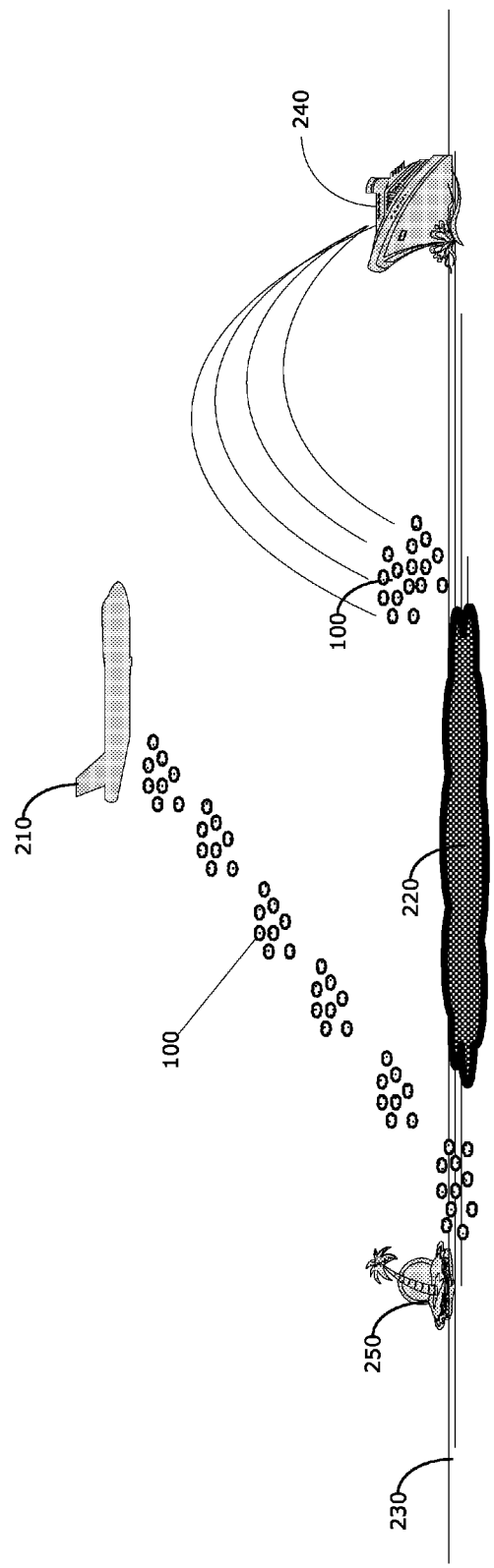
FIG. 2 is a diagram illustrating various methods of deploying an embodiment of the invention.

Referring now to FIG. 2, a diagram illustrates various methods of deploying remediation agent 100. In one method of deployment, an aircraft 210 (e.g. airplane, helicopter, or balloon) is shown dropping remediation agent 100 onto algae bloom 220 at the surface of the ocean 230. In another method, a ship 240 is shown dispersing remediation agent 100 by propelling the remediation agent 100 onto the algae bloom 220. Although the remediation agent 100 is shown being propelled over the side of the ship 240, a simpler method of dropping the remediation agent 100 overboard may be used, such as by a spreading mechanism or by hand, to achieve similar results. One or more of these and other methods of deploying remediation agent 100 may be used together or individually on algae blooms.

In FIG. 2, a sensitive eco-system 250 is endangered by the encroaching algae bloom 220. Aircraft 210 may drop remediation agent 100 directly on the algae bloom 220 and/or onto the sensitive eco-system 250. Alternatively, remediation agent 100 may be manually applied onto algae blooms adjacent to land by such methods as by hand, wheeled spreaders (e.g., a fertilizer spreader), dump trucks or spreading trucks. Remediation agent 100 is more environmentally friendly than algaecides and will biodegrade, thus deploying remediation agent 100 directly onto the sensitive eco-system 250 is a viable option.

Methods of deployment may require consideration of several factors, such as type of algae, location of the algae bloom, and amount of area covered by the algae bloom. For example, larger algae blooms closer to shore may be more efficiently treated using shipboard deployment of the remediation agent 100.

Aerial dispersal over wide areas may be accomplished with equipment similar to that used for dispersing flame retardants or fertilizer. A low flying fixed wing aircraft 210 or helicopter may be used to accurately target dispersal areas. Aircraft 210 may be capable of deploying the remediation agent 100 to remote areas not readily accessible to vehicles or by foot. Furthermore, aircraft may be capable of reaching a target site faster than other dispersal methods, possibly preventing or mitigating harm to sensitive eco-system 250.

Targeting Different Algae Types

Although red tides are infamous, they are but one of the many types of harmful algae blooms (HABs). Some algae blooms are harmful at low concentrations because the algae involved produces dangerous neurotoxins. Other HABs such as macroalgae may not seem harmful, but reduces the biodiversity of a habitat. For example, the macroalgae *Caulerpa* spp. (seaweed) may dominate a coral reef, reducing not only the plant life on the coral reef but also the marine life that depends on the biodiversity of coral reefs.

Algae have evolved to take advantage of different frequencies of light that filter through the aquatic depths. Different types of algae may thrive at different depths. Green algae may dominate at the upper layer just below the surface. Brown and golden algae occupy the middle layers and red algae the bottom layer. There are exceptions to these rules, but in general different algae types exist at different depths.

Figure 3:
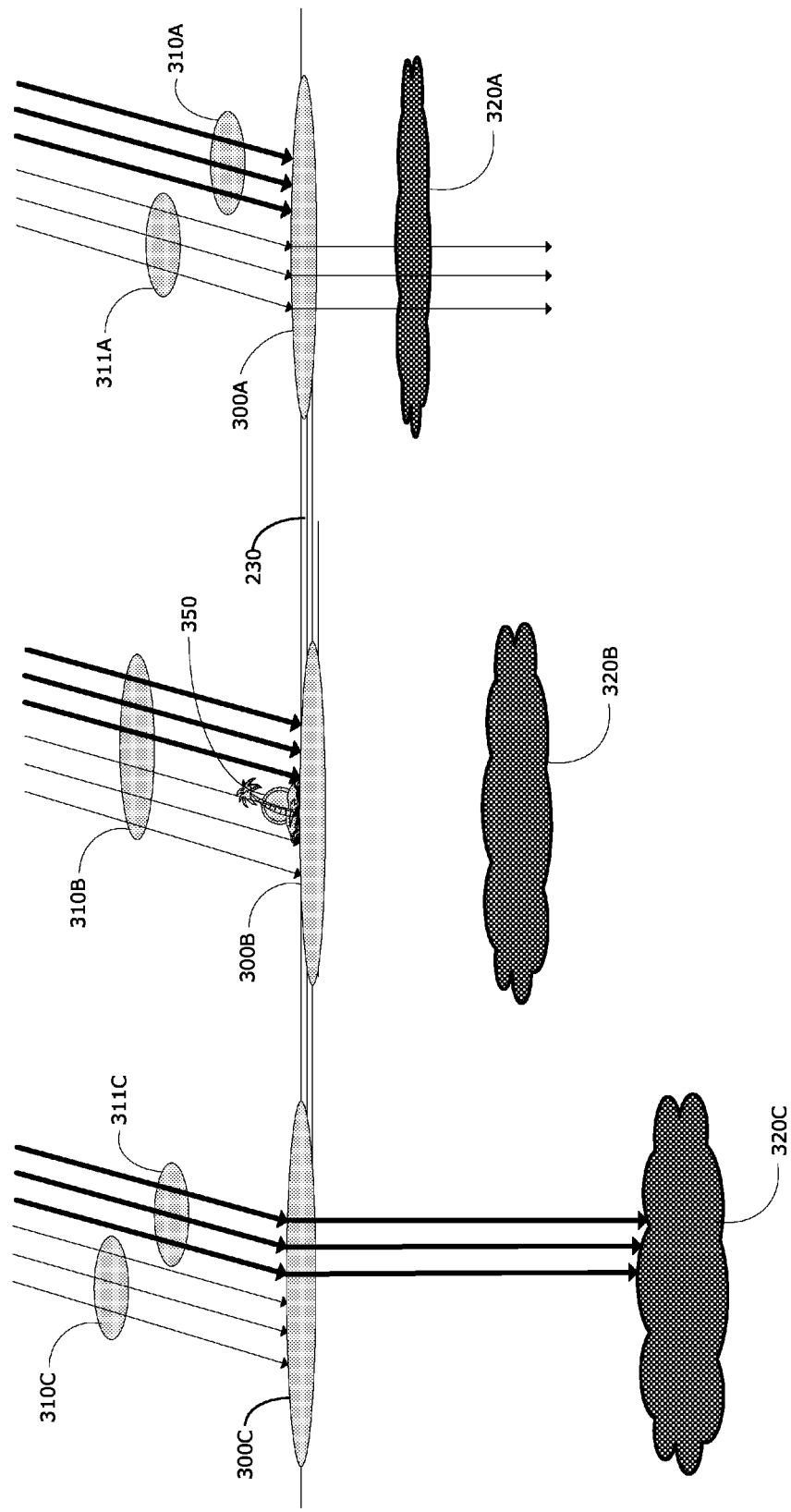
FIG. 3 is a diagram illustrating embodiments of the invention containing different light absorbing compounds.

Referring now to FIG. 3, alternate embodiments of the invention are illustrated to address different types of algae. The embodiments depicted in FIG. 3, differ by the type of light absorbing compound 120 (not shown in FIG. 3, see FIG. 1) each contains. Light absorbing compound 120 filters light out from reaching algae bloom 320A. The light absorbing compound 120 may be selected to absorb light in a range of wavelengths narrower than the range of wavelengths corresponding to the visible spectrum. For example, remediation agent 300A may contain a light absorbing compound 120 that predominantly absorbs light frequencies in the red and yellow ranges, shown as light 310A. Light 311A of a different wavelength is allowed to pass through remediation agent 300A. Remediation agent 300B may contain a different light absorbing compound 120 that absorbs the entire spectrum of visible light or at least a large portion of the visible spectrum to filter light out. Remediation agent 300C may be adapted to absorb light frequencies in the blue and green range. Light 311C of other wavelengths may pass through remediation agent 300C.

Different types of light absorbing compound 120 may be mixed together in remediation agent 100. For example, a light absorbing compound 120 absorbing primarily red light may be mixed with a light absorbing compound 120 absorbing primarily blue light. Such an embodiment of remediation agent 100 may be advantageous in combating algae blooms where the algae can change photosynthetic pigments. Alternatively, instead of light absorbing compound, a biodegradable chemical compound with light absorbing properties may be added to protein product 110.

It may be advantageous to have remediation agent 100 absorb different wavelengths of light. Algae are naturally occurring phytoplankton. Indiscriminately killing off all algae in an area may be harmful to the environment. Adapting the remediation agent 100 to absorb a narrower range of light wavelengths, allows the algae bloom to be targeted with less impact on other types of algae or other plant life.

Figure 4A:
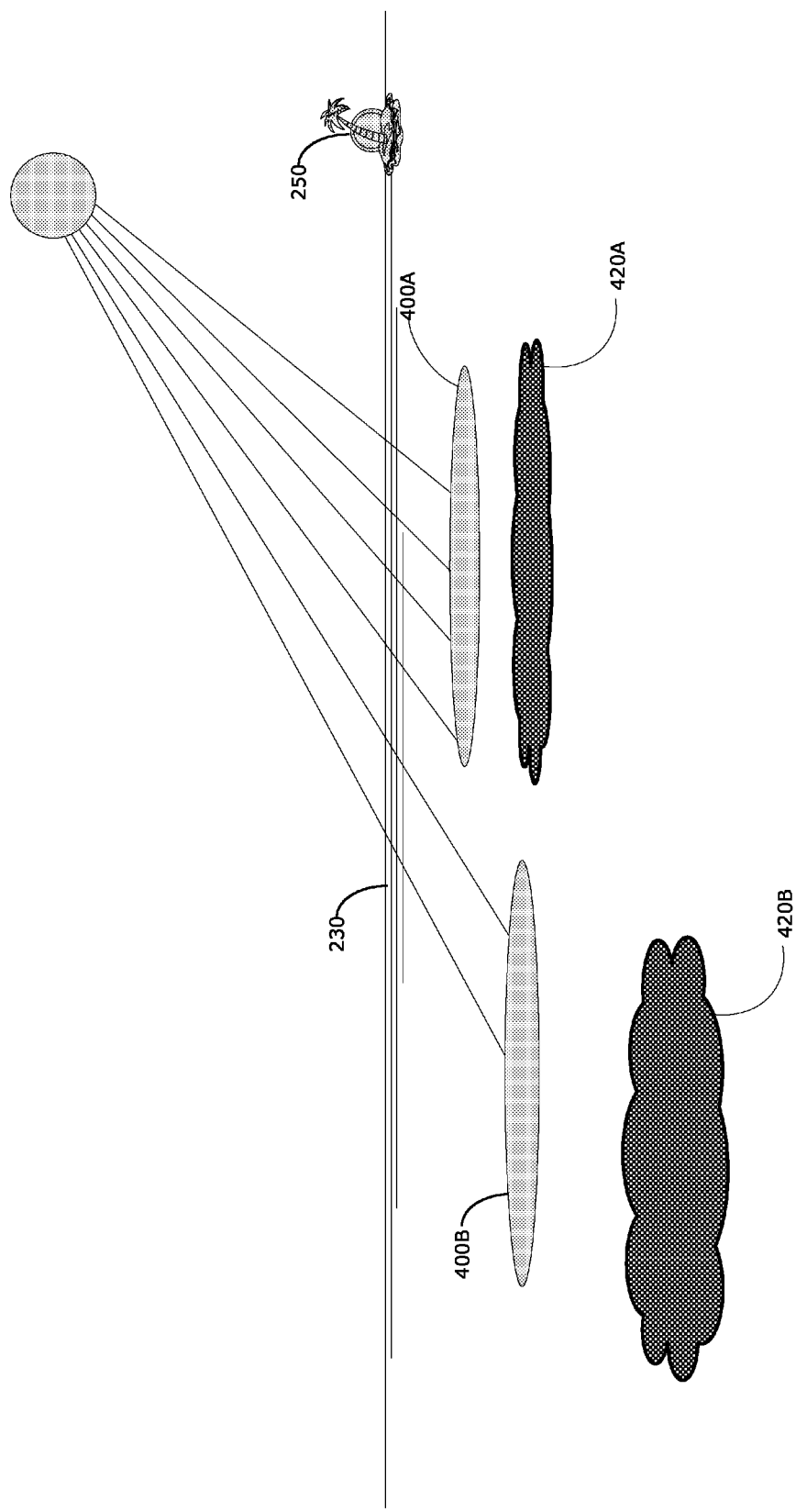
FIG. 4A is an illustration of various embodiments of the invention being used at different water depths.

Referring now to FIG. 4A, a method and agent of targeting algae blooms at different depths is illustrated. In order to combat submerged algae 420A-420B, an inert material 140 (e.g. sand, silt, dirt, etc.) (see FIG. 1) with a specific gravity greater than water (e.g., specific gravity of fresh water in the case of fresh water algae bloom or specific gravity of salt water in the case of a salt water algae bloom) may be used to sink the remediation agents 400A-400B towards algae blooms below the surface of the water 230. The closer the remediation agent, the more light may be filtered away from the algae bloom.

Remediation agent 400A and 400B are alternative embodiments of remediation agent 100 that sink to different depths of water. The buoyancy of remediation agent 400A may be altered so that the remediation agent 400A is slightly denser than surface temperature water. Generally, water is colder the deeper it gets. Colder water is denser than warm water. Thus at some level, the remediation agent 400A will stop sinking. Remediation agent 400B may be made relatively heavier than remediation agent 400A to sink to an even lower depth. These alternative embodiments may be created by adding to the remediation agent 100, an inert material 140 with a specific gravity greater than water. Alternative embodiments of the remediation agent 400A and 400B may or may not include air pockets 130 in their makeup to achieve a desired buoyancy and depth below the water surface.

The amount of remediation agent 100 to be deployed depends on several factors. Sufficient remediation agent 100 should be dispersed to substantially cover the algae bloom to block out selected ranges of wavelengths of light. The concentration or packing density of the flakes or particles of remediation agent 100 comprising the covering layer of remediation agent 100 may determine how much photosynthesis is inhibited and amounts of algae that are killed off. Generally the thicker or more concentrated the covering layer of remediation agent 100, a larger amount of light will be absorbed. The thickness of the covering layer may be affected by the thickness of the individual flakes, with thicker flakes generally forming thicker covering layers and absorbing more light. More light absorption generally inhibits more photosynthesis, thereby destroying larger amounts of algae.

Figure 4B:
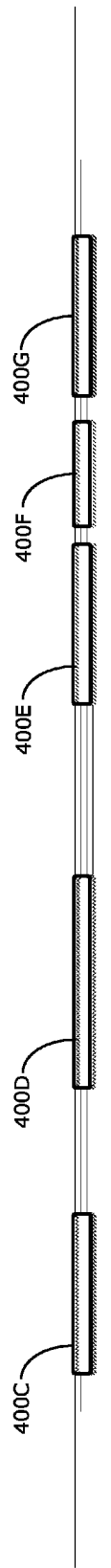
FIG. 4B is a side view illustration of an embodiment of the invention dispersed at different concentrations.

Referring now to FIG. 4B, embodiments of the invention may be deployed at different concentrations upon the surface or at different concentrations below the surface of water. FIG. 4B illustrates remediation agents 400C and 400D shown being deployed at a first concentration upon the surface of the water. Remediation agents 400E through 400G are shown being deployed at a second concentration upon the surface of the water that is greater than the first concentration as there is less space between the particles. The concentration or packing density is initially affected by how many particles are deployed in a given area of an algae bloom. The more desirable concentration would effectively achieve a light absorbing sheet on the surface or below the surface of the water. Subsequent natural effects (e.g., waves, currents, wind,) and man made effects (e.g., boat wake, propeller wash, or machine stirring or dispersing) may disperse remediation agent 100 and reduce its density at the surface of water or at depths in the water.

CONCLUSION

While this specification includes many specifics, these should not be construed as limitations on the scope of the disclosure or of what may be claimed, but rather as descriptions of features specific to particular implementations of the disclosure. Certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. Accordingly, the claimed invention is limited only by the claims that follow below.

What is claimed is:

1. A method of remediation of an algae bloom, the method comprising:
    examining an algae bloom to determine borders of an area of the algae bloom;
    selecting a first deployment means for a remediation agent, the remediation agent including a light absorbing compound suspended in a biodegradable semi-soluble casein product to inhibit photosynthesis in the algae; and
    with the first selected deployment means, deploying the remediation agent over the area of the algae bloom to cover the algae bloom.

2. The method of claim 1, further comprising:
    suspending a light absorbing compound in the biodegradable protein product to absorb a predetermined range of wavelengths of light.

3. The method of claim 1, further comprising:
    suspending a gas in pockets within the semi-soluble casein product to adjust the buoyancy of the remediation agent towards a surface of water.

4. The method of claim 3, wherein
    the gas is one or more of air, nitrogen, helium, hydrogen, oxygen, methane, and ammonia.

5. The method of claim 1, further comprising:
    suspending an inert material with a specific gravity greater than water within the semi-soluble casein product to adjust the buoyancy of the remediation agent down away from a surface of water.

6. The method of claim 1, wherein
    the deployment means is one or more of a spreader, a truck, a ship, and an airplane.

7. The method of claim 3, wherein
    the water is fresh water.

8. The method of claim 3, wherein
    the water is salt water.

9. A method of remediation of an algae bloom, the method comprising:
    deploying a remediation agent over an area of the algae bloom in water, the remediation agent including a light absorbing compound suspended in a biodegradable semi-soluble casein product to inhibit photosynthesis in the algae;

receiving light into the biodegradable semi-soluble casein product in the water;

absorbing light in a predetermined range of wavelengths with the light absorbing compound in the biodegradable semi-soluble casein product to inhibit algae in an algae bloom; and dissolving the biodegradable semi-soluble casein product into the water after a predetermined period of time.

\* \* \* \* \*